(12) United States Patent
Moon et al.

(10) Patent No.: US 10,413,386 B2
(45) Date of Patent: Sep. 17, 2019

(54) HYBRID ORTHODONTIC APPLIANCE

(71) Applicants: Won Moon, Los Angeles, CA (US); Ehab Abdelbar, Los Angeles, CA (US); Paul Kim, Diamond Bar, CA (US)

(72) Inventors: Won Moon, Los Angeles, CA (US); Ehab Abdelbar, Los Angeles, CA (US); Paul Kim, Diamond Bar, CA (US)

( * ) Notice: Subject to any disclaimer, the term of this patent is extended or adjusted under 35 U.S.C. 154(b) by 0 days.

(21) Appl. No.: 15/914,929

(22) Filed: Mar. 7, 2018

(65) Prior Publication Data

US 2019/0231485 A1 Aug. 1, 2019

Related U.S. Application Data

(60) Provisional application No. 62/624,279, filed on Jan. 31, 2018.

(51) Int. Cl.
 *A61C 3/00* (2006.01)
 *A61C 7/10* (2006.01)
 *A61C 7/08* (2006.01)

(52) U.S. Cl.
 CPC . *A61C 7/10* (2013.01); *A61C 7/08* (2013.01)

(58) Field of Classification Search
 CPC .................. A61C 7/10; A61C 7/08
 See application file for complete search history.

(56) References Cited

U.S. PATENT DOCUMENTS

| | | | |
|---|---|---|---|
| 3,699,656 A | 10/1972 | Scheu | |
| 3,724,075 A | 4/1973 | Kesling | |
| 4,299,568 A | 11/1981 | Crowley | |
| 4,413,978 A | 11/1983 | Kurz | |
| 4,553,549 A | 11/1985 | Pope et al. | |
| 4,597,738 A | 7/1986 | Sander et al. | |
| 5,037,295 A * | 8/1991 | Bergersen | A61C 7/08 433/6 |
| 5,055,039 A * | 10/1991 | Abbatte | A61C 7/08 433/24 |
| 5,096,416 A * | 3/1992 | Hulsink | A61C 7/08 433/6 |
| 5,145,364 A | 9/1992 | Martz et al. | |
| 5,376,001 A * | 12/1994 | Tepper | A61C 7/00 433/6 |
| 5,975,893 A | 11/1999 | Chishti et al. | |
| 6,450,807 B1 | 9/2002 | Chishti et al. | |
| 7,328,705 B2 * | 2/2008 | Abramson | A61F 5/566 128/206.11 |
| 7,357,633 B2 * | 4/2008 | Mailyan | A61C 7/10 433/7 |
| 7,661,955 B2 * | 2/2010 | Da Cruz | A61C 7/10 433/18 |
| 7,878,803 B2 * | 2/2011 | Mailyan | A61C 7/00 433/24 |

(Continued)

OTHER PUBLICATIONS

Moon, Won, Restriction Requirement for U.S. Appl. No. 15/914,932, filed Mar. 7, 2018, dated May 18, 2018, 8 pgs.

(Continued)

*Primary Examiner* — Nicholas D Lucchesi (74) *Attorney, Agent, or Firm* — Taylor English Duma LLP (57) ABSTRACT

Provided herein is an orthodontic hybrid appliance for moving one or more teeth of a patient and methods of making and using the same.

27 Claims, 3 Drawing Sheets

(56) References Cited

U.S. PATENT DOCUMENTS

| | | | |
|---|---|---|---|
| 7,955,075 B2* | 6/2011 | Mailyan | A61C 7/10 433/6 |
| 7,975,701 B2 | 7/2011 | Bergersen | |
| 8,062,031 B2* | 11/2011 | Inman | A61C 7/10 433/18 |
| 8,133,050 B2 | 3/2012 | Bergersen | |
| 8,192,196 B2* | 6/2012 | Singh | A61F 5/566 433/7 |
| 8,371,309 B2* | 2/2013 | Diers | A61F 5/566 128/848 |
| 8,414,291 B1 | 4/2013 | Jamilian et al. | |
| 8,474,462 B2* | 7/2013 | Makower | A61F 5/566 128/848 |
| 8,870,566 B2 | 10/2014 | Bergersen | |
| 9,011,145 B2* | 4/2015 | Hang | A61C 7/10 433/7 |
| 9,314,320 B2 | 4/2016 | Urbanek | |
| 9,351,810 B2 | 5/2016 | Moon | |
| D777,929 S* | 1/2017 | Showkatbakhsh | D24/180 |
| 9,585,732 B2* | 3/2017 | Piancino | A61C 7/00 |
| 2004/0013993 A1* | 1/2004 | Ito | A61C 7/00 433/6 |
| 2004/0209218 A1* | 10/2004 | Chishti | A61C 7/00 433/6 |
| 2005/0069834 A1* | 3/2005 | Inman | A61C 7/10 433/18 |
| 2006/0185679 A1 | 8/2006 | Costigan et al. | |
| 2006/0216670 A1 | 9/2006 | Leichtung | |
| 2007/0184398 A1* | 8/2007 | Cronauer | A61C 7/00 433/6 |
| 2008/0227048 A1 | 9/2008 | Tjikueni | |
| 2008/0268400 A1* | 10/2008 | Moss | A61C 7/00 433/24 |
| 2010/0068671 A1* | 3/2010 | Kakavand | A61C 7/08 433/6 |
| 2010/0183997 A1 | 7/2010 | Darendeliler | |
| 2011/0027743 A1 | 2/2011 | Cinader, Jr. et al. | |
| 2011/0236847 A1 | 9/2011 | Hang | |
| 2011/0236849 A1 | 9/2011 | Pogorelsky | |
| 2012/0129117 A1 | 5/2012 | McCance | |
| 2013/0089828 A1 | 4/2013 | Borovinskih | |
| 2013/0230819 A1 | 9/2013 | Arruda | |
| 2014/0302448 A1* | 10/2014 | Cassalia | A61C 7/28 433/9 |
| 2014/0302451 A1* | 10/2014 | Berry | A61C 7/10 433/18 |
| 2015/0125802 A1* | 5/2015 | Tal | A61C 7/10 433/6 |
| 2015/0157421 A1* | 6/2015 | Martz | A61C 7/08 433/6 |
| 2015/0216627 A1* | 8/2015 | Kopelman | A61C 7/08 433/6 |
| 2015/0257856 A1* | 9/2015 | Martz | A61C 7/14 433/6 |
| 2015/0265376 A1* | 9/2015 | Kopelman | A61C 7/08 433/6 |
| 2016/0081767 A1 | 3/2016 | Metcalf et al. | |
| 2016/0081768 A1 | 3/2016 | Kopelman et al. | |
| 2016/0120620 A1 | 5/2016 | Tairaku | |
| 2016/0128803 A1* | 5/2016 | Webber | A61C 7/08 433/6 |
| 2016/0310236 A1* | 10/2016 | Kopelman | A61C 7/002 |
| 2017/0007367 A1 | 1/2017 | Li et al. | |
| 2017/0007387 A1 | 1/2017 | Cohen et al. | |
| 2017/0079747 A1 | 3/2017 | Graf et al. | |
| 2017/0105817 A1 | 4/2017 | Chun | |
| 2017/0156821 A1* | 6/2017 | Kopelman | A61C 7/10 |
| 2017/0156823 A1* | 6/2017 | Roein Peikar | A61C 7/145 |
| 2017/0304108 A1 | 10/2017 | Simonetti | |
| 2017/0367791 A1* | 12/2017 | Raby | A61C 7/002 |
| 2018/0049846 A1* | 2/2018 | Martz | A61C 7/14 |
| 2018/0055602 A1* | 3/2018 | Kopelman | A61C 7/08 |
| 2019/0046298 A1* | 2/2019 | Cinader, Jr. | A61C 7/28 |

OTHER PUBLICATIONS

Moon, Won; Non-Final Office Action for U.S. Appl. No. 15/914,932, filed Mar. 7, 2018, dated Jul. 13, 2018, 14 pgs.

Moon, Won, Restriction Requirement for U.S. Appl. No. 15/914,935, filed Mar. 7, 2018, dated Jun. 25, 2018, 7 pgs.

Moon, Won; International Search Report and Written Opinion for PCT/US2019/015632, filed Jan. 29, 2019 dated Mar. 4, 2019, 8 pgs.

Moon, Won; Non-Final Office Action for U.S. Appl. No. 15/914,932, filed Mar. 7, 2018, dated Mar. 21, 2019, 12 pgs.

Moon, Won; Final Office Action for U.S. Appl. No. 15/914,932, filed Mar. 7, 2018, dated Jan. 28, 2019, 18 pgs.

Moon, Won; Applicant Initiated Interview Summary for U.S. Appl. No. 15/914,932, filed Mar. 7, 2018, dated Feb. 21, 2019, 15 pgs.

Moon, Won; International Search Report for Serial No. PCT/US2019/015647, filed Jan. 29, 2019, dated Feb. 28, 2019, 8 pgs.

Moon, Won; Invitation to Pay Additional Fees for serial No. PCT/US19/15639, filed Jan. 29, 2019, dated Apr. 12, 2019, 2 pgs.

Moon, Won; Non-Final Office Action for U.S. Appl. No. 15/914,935, filed Mar. 7, 2018, dated Sep. 26, 2018, 30 pgs.

* cited by examiner

HYBRID ORTHODONTIC APPLIANCE

FIELD OF THE INVENTION

The present invention generally relates to the field of orthodontics, and in particular to the use of a hybrid orthodontic appliance, and methods of making and using the same.

BACKGROUND OF THE INVENTION

Orthodontic tooth movement is accomplished by fixed and/or removable appliances. One type of appliances that is gaining popularity is orthodontic aligners or clear aligners. Clear aligners are a type of removable appliances used to move the teeth by having the patient wear the said aligner for 1-2 weeks and then switching to another sequential tray where they wear it for 1-2 weeks and so on and so forth.

Clear aligners are fabricated by thermoforming a heat sensitive clear plastic sheet onto a dental model of the teeth. In the aforementioned dental model, the teeth are shifted by a small increment in position and orientation. The concept is that the when the patient wears the plastic trays they will flex and distort and apply force to the teeth forcing them into a new position similar to the dental model used to fabricate the tray. The process is repeated for the number of trays needed to place the teeth in a final position prescribed by a treating doctor or orthodontist. A well-known example is Invisalign®, a polymer-based aligner based on U.S. Pat. No. 5,975,893 (Chishti et al.) and other related patents.

However, there are many areas where aligners are deficient, these areas include and are not limited to:

1) Extraction cases: In extraction cases crowding resolved by extraction of teeth. Usually a premolar is extracted from each quadrant to create enough room to align the remaining teeth. The overall amount of teeth movement is usually quite significantly larger than non-extraction cases. Aligners are usually not suitable for extraction cases and usually orthodontist would use edgewise appliances comprised of braces and arch wires to move the teeth in extraction cases.
2) Cases requiring expansion of the upper and/or lower arches are usually treated using either a specialized expansion device (Quad-helix, bi-helix, active TPA (trans-palatal arch), or hyrax expanders) followed by either edgewise appliance (brackets and arch wires) or aligners. Sometimes expansion can be accomplished using only brackets and heavy arch wires to achieve the expansion.
3) Cases requiring molar uprighting. Uprighting molars requires a great amount of force and cannot be achieved with traditional aligners.
4) Root Movement in general cannot be achieve properly with aligners.
5) Aligners made of plastic cannot exert the amount of force necessary to achieve expansion in the upper and lower arches and are not effective for treatment in the above described areas. Additionally, treatment in these areas requires en-mass movement of distinctive group of teeth, which causes treating using conventional clear aligners difficult, if not impossible.
6) Therefore, there is a need for aligners that overcome the aforementioned short-comings of the clear aligner.
7) Therefore, the embodiments described below address the above-identified issues and needs.

SUMMARY OF THE INVENTION

In one aspect of the present invention, it is provided a hybrid orthodontic appliance comprising two or more orthodontic aligner segments and one or more orthodontic arch wires, wherein each of the aligner segments exerts an aligning force on one or more teeth of a dental arch, but less than all the teeth of the dental arch, of a patient, and wherein the one or more orthodontic arch wires impart controllability to the appliance and augment properties of the aligner with the properties of orthodontic arch wires, thereby enhancing the effectiveness of the aligner segments for realigning the one or more teeth.

In some embodiments of the invention appliance, optionally in combination with any of the various embodiments disclosed herein, properties of the orthodontic arch wires include strength, flexibility and resilience, and force loading.

In some embodiments of the invention appliance, optionally in combination with any of the various embodiments disclosed herein, the orthodontic arch wires are formed from a material comprising Stainless-Steel (SS), TMA (titanium molybdenum alloy), or NiTi material. Any biocompatible alloy can be used.

In some embodiments of the invention appliance, optionally in combination with any of the various embodiments disclosed herein, the one or more arch wires are shaped and placed in a design holding together the aligner segments.

In some embodiments of the invention appliance, optionally in combination with any of the various embodiments disclosed herein, the orthodontic arch wires are capable of being in direct contact with the teeth and their surrounding tissue or embedded within the aligner segment(s)

In some embodiments of the invention appliance, optionally in combination with any of the various embodiments disclosed herein, at least one of the aligner segments exerts the aligning force on a single tooth of the dental arch.

In a second aspect of the present invention, it is provided a method of fabrication, comprising providing two or more orthodontic aligner segments, providing one or more orthodontic arch wires, and forming a hybrid appliance comprising the two or more aligner segments and the one or more orthodontic arch wires, wherein each of the aligner segments exerts an aligning force on one or more teeth of a dental arch, but less than all the teeth of the dental arch, of a patient, and wherein the one or more orthodontic arch wires impart controllability to the appliance and augment properties of the aligner with the properties of orthodontic arch wires, thereby enhancing the effectiveness of the aligner segments for realigning the one or more teeth.

In some embodiments of the invention method, optionally in combination with any of the various embodiments disclosed herein, the properties of the orthodontic arch wires include strength, flexibility and resilience, and force loading.

In some embodiments of the invention method, optionally in combination with any of the various embodiments disclosed herein, the orthodontic arch wires are formed from a material comprising Stainless-Steel (SS), TMA (titanium molybdenum alloy), or NiTi material.

In some embodiments of the invention method, optionally in combination with any of the various embodiments disclosed herein, the one or more arch wires are shaped and placed in a design holding together the aligner segments.

In some embodiments of the invention method, optionally in combination with any of the various embodiments disclosed herein, the orthodontic arch wires are capable of being in direct contact with the teeth and their surrounding tissue or embedded within the aligner segment(s).

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner.

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner.

In some embodiments of the invention method, optionally in combination with any of the various embodiments disclosed herein, at least one of the aligner segments exerts the aligning force on a single tooth of the dental arch.

In a further aspect of the present invention, it is provided a method of orthodontic treatment on a patient in need thereof, comprising providing a hybrid orthodontic appliance comprising two or more orthodontic aligner segments and one or more orthodontic arch wires according to a prescription by a treating doctor to move or re-align a one or more teeth of the patient, and applying the hybrid appliance to the patient, wherein each of the aligner segments exerts an aligning force on one or more teeth of a dental arch of a patient, and wherein the one or more orthodontic arch wires impart controllability to the appliance so as to enhance the effectiveness of the aligner segments for realigning the one or more teeth and augment properties of the aligner with the properties of orthodontic arch wires.

In some embodiments of the invention method, optionally in combination with any of the various embodiments disclosed herein, the properties of the orthodontic arch wires include strength, flexibility and resilience, and force loading.

In some embodiments of the invention method, optionally in combination with any of the various embodiments disclosed herein, the orthodontic arch wires are formed from a material comprising Stainless-Steel (SS), TMA (titanium molybdenum alloy), or NiTi material.

In some embodiments of the invention method, optionally in combination with any of the various embodiments disclosed herein, the one or more arch wires are shaped and placed in a design holding together the aligner segments.

In some embodiments of the invention method, optionally in combination with any of the various embodiments disclosed herein, the orthodontic arch wires are capable of being in direct contact with the teeth and their surrounding tissue or embedded within the aligner segment(s).

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner In some embodiments of the invention method, optionally in combination with any of the various embodiments disclosed herein, at least one of the aligner segments exerts the aligning force on a single tooth of the dental arch.

DESCRIPTION OF THE DRAWINGS

FIGS. 2A-2F show various T-shape designs of the loop of the invention hybrid orthodontic appliance shown in FIG. 1.

DETAILED DESCRIPTION OF THE INVENTION

Definitions

As used herein, the term "aligner" is defined as a plastic tray, which can be clear or non-clear, that covers the teeth and guides one or more of the teeth to move from its/their original position(s) to the final position(s) over a period of time as prescribed by a treating doctor, who is also referred to as an "orthodontic doctor" or an "orthodontist". Clear orthodontic appliances refer to those made from a plastic material, which is generally a polyester material. Such clear appliances are exemplified by Invisalign® aligners. The Invisalign® aligners, and methods of making and using the same, are described in general in U.S. Pat. Nos. 6,450,807, and 5,975,893, the teachings of which are incorporated herein by reference in their entirety.

As used herein, the term "original position" of one or more teeth refers to the position of the one or more teeth of the target of treatment prior to the treatment using the appliance of invention; and the term "final position" refers to position of such one or more teeth at the conclusion time point of an orthodontic treatment course prescribed by a treating doctor; and the term "intermediate position" refers to any position between the original position and the final position of the one or more teeth of the target of treatment prescribed by a treating doctor.

As used herein, the term "appliance" refers to an orthodontic device for moving a one or more teeth according to a prescription by a treating doctor.

Hybrid Orthodontic Device

In one aspect of the present invention, it is provided a hybrid orthodontic appliance comprising two or more orthodontic aligner segments and one or more orthodontic arch wires, wherein each of the aligner segments exerts an aligning force on one or more teeth of a dental arch, but less than all the teeth of the dental arch, of a patient, and wherein the one or more orthodontic arch wires impart controllability to the appliance and augment properties of the aligner with the properties of orthodontic arch wires, thereby enhancing the effectiveness of the aligner segments for realigning the one or more teeth.

In some embodiments of the invention appliance, optionally in combination with any of the various embodiments disclosed herein, properties of the orthodontic arch wires include strength, flexibility and resilience, and force loading.

In some embodiments of the invention appliance, optionally in combination with any of the various embodiments disclosed herein, the orthodontic arch wires are formed from a material comprising Stainless-Steel (SS), TMA (titanium molybdenum alloy), or NiTi material.

In some embodiments of the invention appliance, optionally in combination with any of the various embodiments disclosed herein, the one or more arch wires are shaped and placed in a design holding together the aligner segments.

In some embodiments of the invention appliance, optionally in combination with any of the various embodiments disclosed herein, the orthodontic arch wires are capable of being in direct contact with the teeth and their surrounding tissue or embedded within the aligner segment(s).

In some embodiments of the invention appliance, optionally in combination with any of the various embodiments disclosed herein, at least one of the aligner segments exerts the aligning force on a single tooth of the dental arch.

The arch wires are combined with aligner to augment the properties of aligners with the properties of orthodontic arch wires. The arch wire properties include the following:
1) Strength: by using different thicknesses and shapes of the wire the appliance can be made stronger than traditional aligners and can exert a strong force needed for moving molars in expansion and extraction cases;
2) Flexibility and Resilience: opening and closing loops can be added to the wires to increase the flexibility of the appliance. By using different material for the wires and cutting an aligner into two or more aligner segments the overall flexibility and resilience of the appliance can be increased. This insures a more biologically acceptable appliance; and
3) Force loading: the aligner segments can be linked together with different shape and materials of wires to apply forced on different parts of the dental arch. This allows for using a fewer number of trays to achieve certain movements and enough force to achieve tooth movements which may not be possible with traditional aligners.
4) Focus: The invention appliance allows an aligning force to be focused on a selected number of teeth, and sometimes a single tooth, of the dental arch, which is absent in conventional plastic orthodontics. This feature of the invention appliance would allow for a more efficient orthodontic treatment, reducing time and cost of orthodontic treatment.

Figure 1:
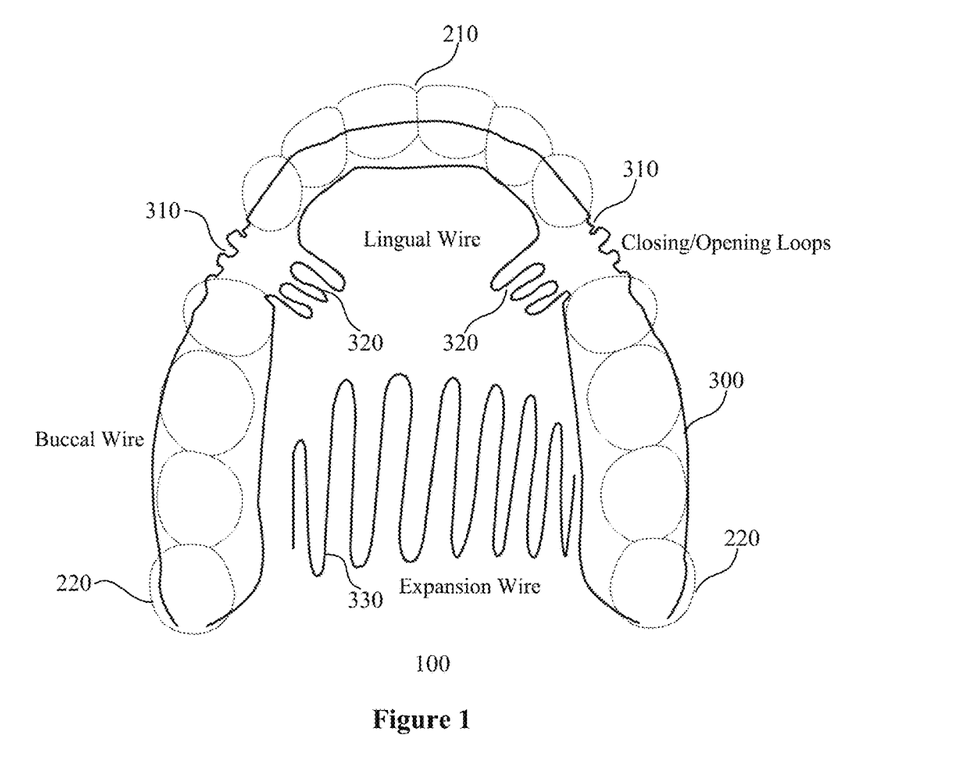
FIG. 1 is an image of an embodiment of the invention hybrid appliance.
Figures 2A, 2F:
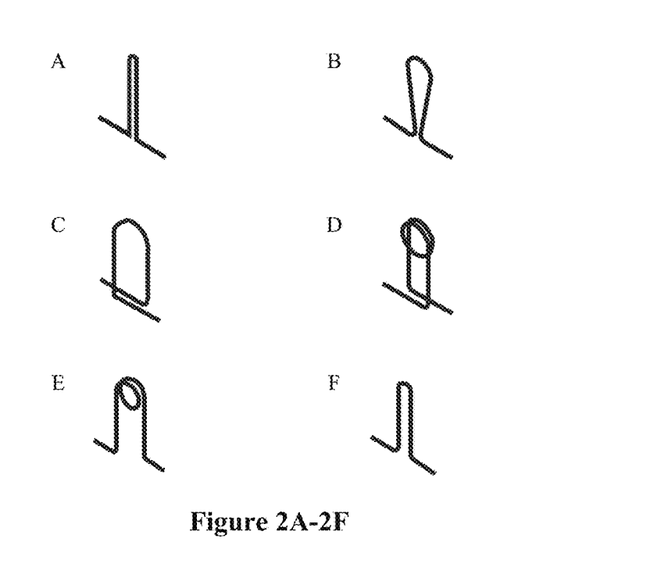

FIG. 1 and FIGS. 2A and 2B show a few embodiments of the invention hybrid orthodontic appliance.

Figure 5A:
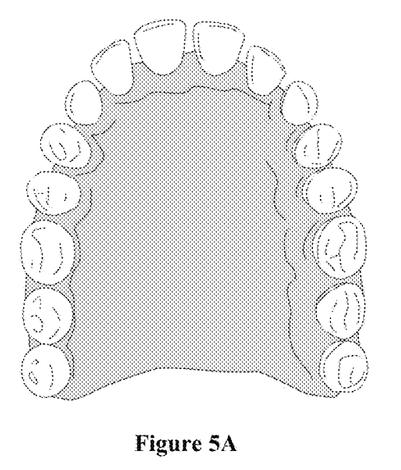
FIGS. 5A-5D illustrate advantages of the invention hybrid appliance over traditional appliances.

FIG. 5A depicts the tooth arch of a patient prior to orthodontic treatment.

Figure 5B:
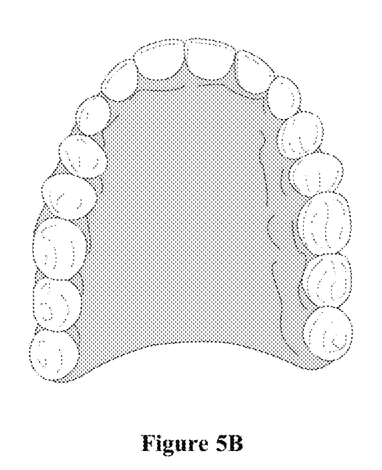

FIG. 5B depicts the tooth arch of a patient post orthodontic treatment.

Figure 5C:
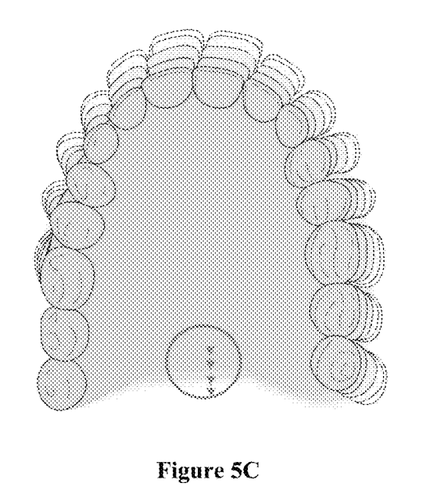

FIG. 5C depicts the many steps required to achieve the result shown by FIG. 5B using traditional aligning appliances.

Figure 5D:
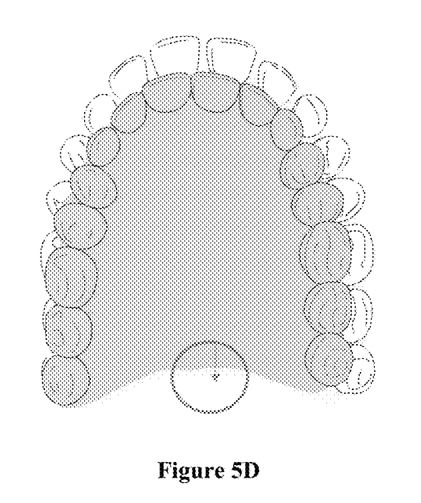

FIG. 5D depicts the many steps required to achieve the result shown by FIG. 5B using the invention hybrid appliances. It is clear that treatment using the invention hybrid appliances requires fewer steps to achieve the result shown by FIG. 5B, which shows the invention hybrid appliances are advantageous.

Method of Fabrication

In a second aspect of the present invention, it is provided a method of fabrication, comprising
providing two or more orthodontic aligner segments,
providing one or more orthodontic arch wires, and
forming a hybrid appliance comprising the two or more aligner segments and the one or more orthodontic arch wires,
wherein each of the aligner segments exerts an aligning force on one or more teeth of a dental arch, but less than all the teeth of the dental arch, of a patient, and
wherein the one or more orthodontic arch wires impart controllability to the appliance and augment properties of the aligner with the properties of orthodontic arch wires, thereby enhancing the effectiveness of the aligner segments for realigning the one or more teeth.

In some embodiments of the invention method, optionally in combination with any of the various embodiments disclosed herein, the properties of the orthodontic arch wires include strength, flexibility and resilience, and force loading.

In some embodiments of the invention method, optionally in combination with any of the various embodiments disclosed herein, the orthodontic arch wires are formed from a material comprising Stainless-Steel (SS), TMA (titanium molybdenum alloy), or NiTi material.

In some embodiments of the invention method, optionally in combination with any of the various embodiments disclosed herein, the one or more arch wires are shaped and placed in a design holding together the aligner segments.

In some embodiments of the invention method, optionally in combination with any of the various embodiments disclosed herein, the orthodontic arch wires are capable of being in direct contact with the teeth and their surrounding tissue or embedded within the aligner segment(s).

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner.

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments. Such different materials can be, for example, Stainless-Steel (SS), TMA (titanium molybdenum alloy), NiTi material, or a combination thereof.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner.

In some embodiments of the invention appliance, optionally in combination with any of the various embodiments disclosed herein, at least one of the aligner segments exerts the aligning force on a single tooth of the dental arch.

Methods of computer aided fabrication of plastic aligner trays are well documented in the art. Examples of such methods are described in U.S. Pat. Nos. 6,450,807, and 5,975,893, the teachings of which are incorporated herein by reference in their entirety.

Method of Use

In a further aspect of the present invention, it is provided a method of orthodontic treatment on a patient in need thereof, comprising
providing a hybrid orthodontic appliance comprising two or more orthodontic aligner segments and one or more orthodontic arch wires according to a prescription by a treating doctor to move or re-align a one or more teeth of the patient, and
applying the hybrid appliance to the patient,
wherein each of the aligner segments exerts an aligning force on one or more teeth of a dental arch of a patient, and
wherein the one or more orthodontic arch wires impart controllability to the appliance so as to enhance the effectiveness of the aligner segments for realigning the one or more teeth and augment properties of the aligner with the properties of orthodontic arch wires.

In some embodiments of the invention method, optionally in combination with any of the various embodiments disclosed herein, the properties of the orthodontic arch wires include strength, flexibility and resilience, and force loading.

In some embodiments of the invention method, optionally in combination with any of the various embodiments disclosed herein, the orthodontic arch wires are formed from a material comprising Stainless-Steel (SS), TMA (titanium molybdenum alloy), or NiTi material.

In some embodiments of the invention method, optionally in combination with any of the various embodiments disclosed herein, the one or more arch wires are shaped and placed in a design holding together the aligner segments.

In some embodiments of the invention method, optionally in combination with any of the various embodiments disclosed herein, the orthodontic arch wires are capable of being in direct contact with the teeth and their surrounding tissue or embedded within the aligner segment(s).

In some embodiments of the invention method, optionally in combination with any of the various embodiments disclosed herein, the orthodontic arch wires comprise open and/or close loops so as to increase the flexibility of the appliance.

In some embodiments of the invention method, optionally in combination with any of the various embodiments disclosed herein, the resilience and/or flexibility of the appliance are modulated by using different materials to form the wires and cutting an aligner into two or more aligner segments. Such different materials can be, for example, Stainless-Steel (SS), TMA (titanium molybdenum alloy), NiTi material, or a combination thereof.

In some embodiments of the invention method, optionally in combination with any of the various embodiments disclosed herein, the pieces of the aligner are tied together with different shape and materials of wires to apply forced on different segments of the dental arch so as to allow for using a fewer number of trays to achieve tooth movements or using the same number of trays to generate a force sufficient to achieve tooth movements which may not be possible with a traditional aligner.

In some embodiments of the invention appliance, optionally in combination with any of the various embodiments disclosed herein, at least one of the aligner segments exerts the aligning force on a single tooth of the dental arch.

The following examples illustrate rather than limit the embodiments of the present invention.

Example 1-2—Hybrid Orthodontic Appliances

Example 1

Figure 3A:
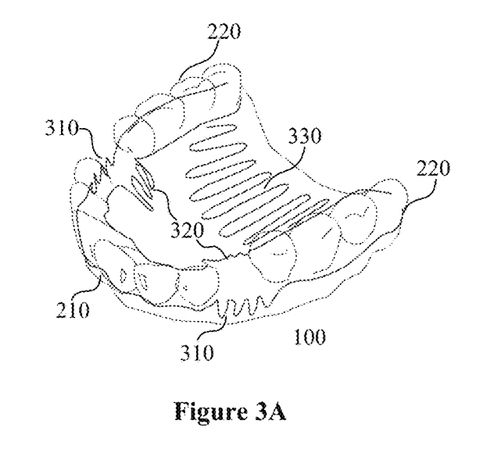
FIGS. 3A and 3B are images of an embodiment of the invention hybrid appliance.
Figure 3B:
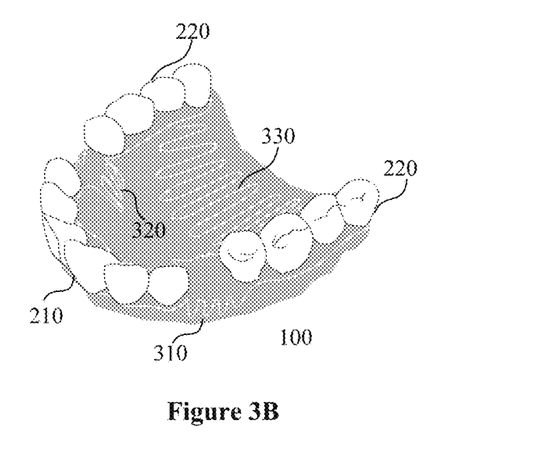

A hybrid orthodontic appliance that includes aligner segments and an arch wire was fabricated, shown in FIG. 1, FIGS. 2A-2F, and FIGS. 3A-3B. Referring to FIG. 1, the hybrid orthodontic appliance 100 includes two aligner segments, a front segment 210 and a back segment 220, and an arch wire 300. The front segment 210 is for exerting an aligning force on the front segment of the dental arch, and the back segment 220 is for exerting an aligning force on the back segment of the dental arch. The arch wire 300 holds together the aligner segments 210 and 220 and includes springs 310 (outside) and 320 (inside) between the front segment 210 and the back segment 220 and a spring 330 (spring expansion wire) between the left side and right side of the back segment 220. Springs 310 and 320 are part of the arch wire structure, and spring 330 is discrete, as shown in FIGS. 1 and 3A. The front part of the arch wire 300 and spring 330 are embedded within the front aligner segment 210 and the back aligner segment 220 (middle part), respectively, shown in FIGS. 1 and 3A-3B.

FIGS. 2A-2F show various T-shape designs of the loop of the invention hybrid orthodontic appliance shown in FIG. 1.

Example 2

Figure 4:
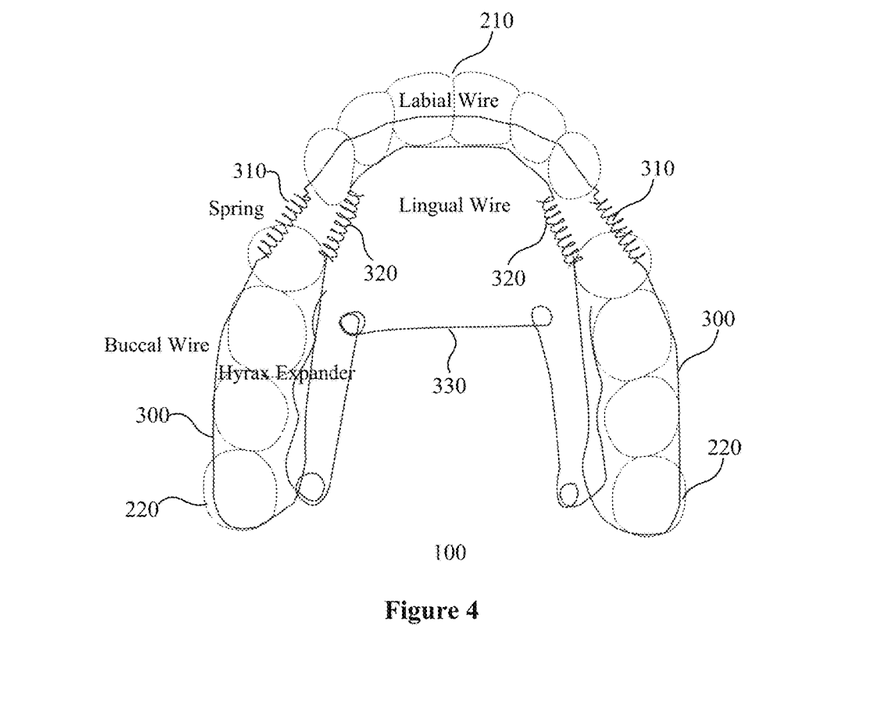
FIG. 4 shows an embodiment of the invention hybrid appliance.

FIG. 4 shows another invention device. Referring to FIG. 4, the hybrid orthodontic appliance 100 includes two aligner segments, a front segment 210 and a back segment 220, and an arch wire 300. The front segment 210 is for exerting an aligning force on the front segment of the dental arch, and the back segment 220 is for exerting an aligning force on the back segment of the dental arch. The arch wire 300 holds together the aligner segments 210 and 220 and includes springs 310 (outside) and 320 (inside) between the front segment 210 and the back segment 220 and a spring 330 (hyrax expander) between the left side and right side of the back segment 220. Springs 310 and 320 are part of the arch wire structure, and spring 330 is discrete.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The teachings of the references, including patents and patent related documents, cited herein are incorporated herein in their entirety to the extent not inconsistent with the teachings herein.

We claim:

1. A hybrid orthodontic appliance comprising two or more orthodontic aligner segments and one or more orthodontic arch wires,
wherein the two or more orthodontic aligner segments are segments of a traditional plastic aligner tray,
wherein each of the aligner segments encloses one or more teeth of a dental arch, but less than all the teeth of the dental arch, of a patient, and exerts an aligning force on the one or more teeth,
wherein the one or more orthodontic arch wires comprise a lingual wire and a labial wire and impart controllability to the appliance and augment properties of the aligner segments with the properties of orthodontic arch wires, thereby enhancing the effectiveness of the aligner segments for realigning the one or more teeth, and
wherein the lingual wire and the labial wire enclose substantially the entire dental arch.

2. The hybrid appliance according to claim 1, wherein properties of the one or more orthodontic arch wires include strength, flexibility and resilience, and force loading.

3. The hybrid appliance according to claim 2, wherein the one or more orthodontic arch wires comprise open and/or close loops so as to increase the flexibility of the appliance.

4. The hybrid appliance according to claim 2, wherein resilience and/or flexibility of the appliance are modulated by using different materials to form the one or more orthodontic wires and cutting an aligner into two or more aligner segments.

5. The hybrid appliance according to claim 1, wherein the one or more orthodontic arch wires are formed from a material comprising Stainless-Steel (SS), TMA (titanium molybdenum alloy), or NiTi material.

6. The hybrid appliance according to claim 1, wherein the one or more arch wires are shaped and placed in a design holding together the aligner segments.

7. The hybrid appliance of claim 6, wherein the aligner segments are linked together with different shape and materials of wires to apply forces on different segments of the dental arch so as to allow for using a fewer number of trays to achieve tooth movements or using the same number of trays to generate a force sufficient to achieve tooth movements.

8. The hybrid appliance according to claim 1, wherein the one or more orthodontic arch wires are capable of being in direct contact with the one or more teeth and their surrounding tissue or embedded within the aligner segments.

9. The hybrid appliance of claim 1, wherein at least one of the aligner segments exerts the aligning force on a single tooth of the dental arch.

10. A method of fabrication, comprising:
providing two or more orthodontic aligner segments, providing one or more orthodontic arch wires, and
forming a hybrid appliance comprising the two or more aligner segments and the one or more orthodontic arch wires,
wherein the two or more orthodontic aligner segments are segments of a traditional plastic aligner tray,
wherein each of the aligner segments encloses one or more teeth of a dental arch, but less than all the teeth of the dental arch, of a patient, and exerts an aligning force on the one or more teeth,
wherein the one or more orthodontic arch wires comprise a lingual wire and a labial wire and impart controllability to the appliance and augment properties of the aligner segments with the properties of orthodontic arch wires, thereby enhancing the effectiveness of the aligner segments for realigning the one or more teeth, and
wherein the lingual wire and the labial wire enclose substantially the entire dental arch.

11. The method according to claim 10, wherein properties of the orthodontic arch wires include strength, flexibility and resilience, and force loading.

12. The method according to claim 11, wherein the one or more orthodontic arch wires comprise open and/or close loops so as to increase the flexibility of the appliance.

13. The method according to claim 10, wherein the one or more orthodontic arch wires are formed from a material comprising Stainless-Steel (SS), TMA (titanium molybdenum alloy), or NiTi material.

14. The method according to claim 11, wherein resilience and/or flexibility of the appliance are modulated by using different materials to form the one or more orthodontic wires and cutting an aligner into two or more aligner segments.

15. The method according to claim 10, wherein the aligner segments comprise 2, 3 or more pieces, and wherein the one or more arch wires are shaped and placed in a design holding together the aligner segments.

16. The method of claim 15, wherein the aligner segments are linked together with different shape and materials of the one or more orthodontic wires to apply forces on different segments of the dental arch so as to allow for using a fewer number of trays to achieve tooth movements or using the same number of trays to generate a force sufficient to achieve tooth movements.

17. The method according to claim 10, wherein the one or more orthodontic arch wires are capable of being in direct contact with the one or more teeth and their surrounding tissue or embedded within the aligner segments.

18. The method of claim 10, wherein at least one of the aligner segments exerts the aligning force on a single tooth of the dental arch.

19. A method of orthodontic treatment on a patient in need thereof, comprising:
providing a hybrid orthodontic appliance comprising two or more orthodontic aligner segments and one or more orthodontic arch wires according to a prescription by a treating doctor to move or re-align a one or more teeth of the patient, and
applying the hybrid appliance to the patient,
wherein the two or more orthodontic aligner segments are segments of a traditional plastic aligner tray,
wherein each of the aligner segments encloses one or more teeth of a dental arch, but less than all the teeth of the dental arch, of a patient, and exerts an aligning force on the one or more teeth,
wherein the one or more orthodontic arch wires comprise a lingual wire and a labial wire and impart controllability to the appliance and augment properties of the aligner segments with the properties of orthodontic arch wires, thereby enhancing the effectiveness of the aligner segments for realigning the one or more teeth, and
wherein the lingual wire and the labial wire enclose substantially the entire dental arch.

20. The method according to claim 19, wherein properties of the one or more orthodontic arch wires include strength, flexibility and resilience, and force loading.

21. The method according to claim 20, wherein the one or more orthodontic arch wires comprise open and/or close loops so as to increase the flexibility of the appliance.

22. The method according to claim 20, wherein resilience and/or flexibility of the appliance are modulated by using different materials to form the one or more wires and cutting an aligner into two or more aligner segments.

23. The method according to claim 19, wherein the one or more orthodontic arch wires are formed from a material comprising Stainless-Steel (SS), TMA (titanium molybdenum alloy), or NiTi material.

24. The method of claim 23, wherein at least one of the aligner segments exerts the aligning force on a single tooth of the dental arch.

25. The method according to claim 19, wherein the aligner segments comprises 2, 3 or more pieces, and wherein the one or more arch wires are shaped and placed in a design holding together the aligner segments.

26. The method of claim 25, wherein the aligner segments are linked together with different shape and materials of the one or more wires to apply forces on different segments of the dental arch so as to allow for using a fewer number of trays to achieve tooth movements or using the same number of trays to generate a force sufficient to achieve tooth movements.

27. The method according to claim 19, wherein the one or more orthodontic arch wires are capable of being in direct contact with the teeth and their surrounding tissue or embedded within the aligner segments.

* * * * *